United States Patent [19]

Watanabe

[11] Patent Number: 4,949,284

[45] Date of Patent: Aug. 14, 1990

[54] METHOD OF ADJUSTING DENSITY MEASUREMENT POSITION

[75] Inventor: Hideo Watanabe, Ibaraki, Japan

[73] Assignee: Komori Printing Machinery, Co., Tokyo, Japan

[21] Appl. No.: 134,696

[22] Filed: Dec. 18, 1987

[30] Foreign Application Priority Data

Feb. 3, 1987 [JP] Japan .................................. 62-21879

[51] Int. Cl.⁵ .......................................... G06F 15/626
[52] U.S. Cl. .................... 364/520; 364/518; 356/444; 101/365
[58] Field of Search ............... 364/519, 551, 520, 518; 358/80; 356/401, 443, 444, 445, 448, 375; 340/706; 101/365

[56] References Cited

U.S. PATENT DOCUMENTS

| | | | |
|---|---|---|---|
| 4,489,652 | 12/1984 | Takeuchi et al. | 101/211 |
| 4,518,862 | 5/1985 | Dorn | 250/561 |
| 4,546,700 | 10/1985 | Kishner et al. | 101/211 |
| 4,596,468 | 6/1986 | Simeh | 356/400 |
| 4,679,071 | 7/1987 | Kitagawa | 358/75 |
| 4,699,515 | 10/1987 | Tamimoto et al. | 356/40 |
| 4,701,053 | 10/1987 | Ikenaga | 356/375 |
| 4,717,954 | 1/1988 | Fujita et al. | 358/80 |
| 4,755,750 | 7/1988 | Leuschner | 324/158 R |
| 4,764,880 | 8/1988 | Pearl | 364/519 |
| 4,811,239 | 3/1989 | Tsao | 364/519 |

Primary Examiner—Gary V. Harkcom
Assistant Examiner—Phu K. Nguyen
Attorney, Agent, or Firm—Blakeley, Sokoloff, Taylor & Zafman

[57] ABSTRACT

A density measurement position adjustment method includes the steps of setting a reference sheet on which a predetermined pattern is printed on an X-Y coordinate table, designating at least three reference points within the pattern of the reference sheet, determining coordinate positions on the X-Y coordinate table of the three reference points, and memorizing coordinate positions at density measurement reference points within the pattern of the reference sheet with a single point and two intersecting lines obtained by computation based on the coordinate positions of the reference points being as an origin, an X-axis and a Y-axis, respectively. This method further includes the steps of setting a sample sheet on which the same pattern as the pattern on the reference sheet is printed on the X-Y coordinate table, detecting coordinate positions on the X-Y coordinate table of corresponding reference points within the pattern on the sample sheet, determining a detection origin, a detection X-axis and a detection X-axis by computation based on the coordinate positions of the corresponding reference points on the sample sheet, and correcting coordinate positions of density measurment points, which correspond to the density measurement points on the reference sheet, within the pattern on the sample sheet so that the detection origin, detection X-axis and detection Y-axis are in correspondence with the origin, X-axis and Y-axis, respectively.

27 Claims, 8 Drawing Sheets

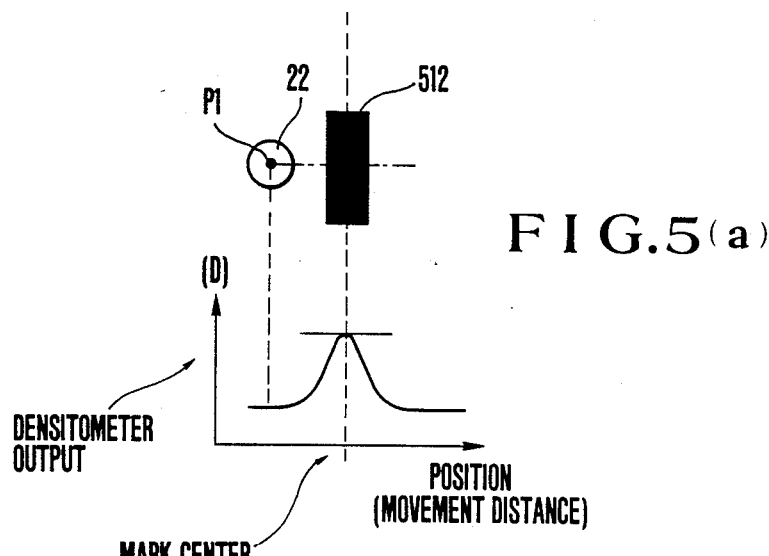
FIG.5(a)
FIG.5(b)
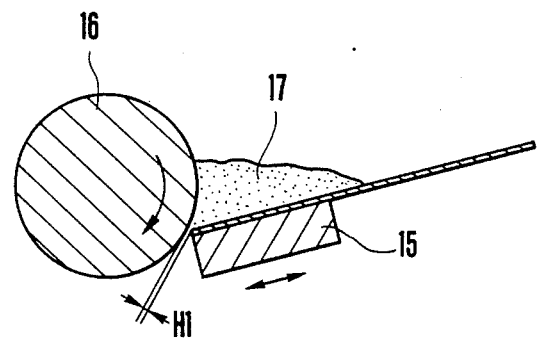
FIG.7

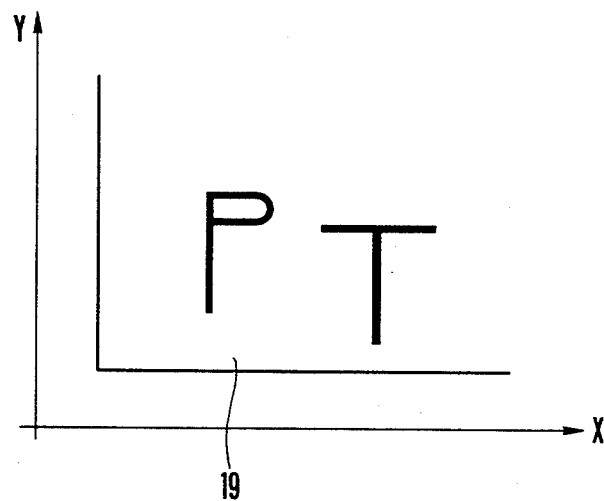
F I G. 11

METHOD OF ADJUSTING DENSITY MEASUREMENT POSITION

BACKGROUND OF THE INVENTION

The present invention relates to a method for adjusting density measurement positions by making use of changes in densities measured by a scanning densitometer, and more particularly to a density measurement position adjustment method suitable when used in order to allow coordinate positions of density measurement points of a sample sheet placed on an X-Y table to be in correspondence with coordinate positions of density measurement reference points of a reference sheet.

In a process for a printing work, a quantity of an ink supplied has been conventionally controlled with a view to checking a sample sheet on which a pattern is printed to maintain the density of the pattern at a predetermined density. Ordinarily, as shown in FIG. 12, on a sample sheet 42, a belt-shaped solid mark 41 having a predetermined width W is printed at the paper end portion at the same process as that for a picture print 40. Densities of respective colors assigned to sections obtained by dividing the solid mark 41 in a length direction are measured. Namely, there is adopted a method to adjust the solid mark 41 of the sample sheet 42 to a predetermined position on the basis of the judgment by the eye, or to cause the paper end of the sample sheet to be in contact with a guide to thereby position and arrange the sample sheet 42 on a table, thus allowing a head unit of a densitometer to scan thereabove to measure densities of respective colors. In this instance, the density of the pattern 40 is represented by the density of the solid mark 41. In such a density measurement method, it is sufficient that the density measurement area of the head unit of the densitometer falls within the width W of the solid mark 41. Since setting is generally made such that the solid mark 41 is broader than the density measurement area of the head unit, the position adjustment is easy.

In accordance with such a conventional density measurement method, however, while the position adjustment is easy, the drawback therewith is that direct control or supervision of a picture is impossible because the density of the picture is represented by the density of the solid mark. Namely, there may occurs an inconvenience such that the density of an actual pattern fails to clear a prescribed density although the density of the solid mark clears the prescribed density For directly controlling the density of a pattern, it is required to allow a desired density measurement point (density measurement reference point) of, e.g., a reference sheet, i.e., a specimen sheet on which a pattern satisfying a prescribed density is printed to be precisely in correspondence with a density measurement point of a sample sheet corresponding to the above-mentioned measurement reference point. Namely, when an attempt is made to directly control the density of a pattern, differently from the method to scan a solid mark, there is the possibility that a slight aberation or deviation of a measurement position leads to a large density measurement error. Since the positional relationship between the paper end and the pattern is not necessarily fixed, problem is likely to occur in the adjustment of position of a sample sheet along the guide. Because precision is required for the position adjustment based on the judgment by the eye, its workability is extremely poor.

SUMMARY OF THE INVENTION

With the above in view, an object of the present invention is to provide a density measurement position adjustment method to allow, with a lessened burden on an operator, coordinate positions of density measurement reference points on a reference sheet to be extremely precisely in correspondence with coordinate positions of density measurement points on a sample sheet, thus making it possible to directly control the density of a pattern.

Another object of the present invention is to provide, a density measurement position adjustment method in which a broader solid mark as used in the prior art is not used, thereby making it possible to save printing papers accordingly.

The above-mentioned objects are achieved by a density measurement position adjustment method including the steps of: setting a reference sheet on which a predetermined pattern is printed on an X-Y coordinate table; designating at least three reference points referred to as first to third reference points within the pattern of the reference sheet; determining coordinate positions on said X-Y coordinate table of said three reference points; computating a single point and two intersecting lines based on said coordinate positions of said reference points being as an origin, an X-axis and a Y-axis, respectively; memorizing coordinate positions at density measurement reference points within said pattern of said reference sheet on a coordinate table set by using said single point and two intersecting lines; setting a sample sheet on which the same pattern as the pattern on the reference sheet is printed on the X-Y coordinate table; detecting coordinate positions on the X-Y coordinate table of points, which correspond to the three reference points on the reference sheet, within the pattern on the sample sheet; determining a detection origin, a detection X-axis and a detection Y-axis by computation based on the coordinate positions of the points on the sample sheet; and correcting coordinate positions of density measurement points, which correspond to the density measurement points on the reference sheet, within the pattern on the sample sheet so that the detection origin, detection X-axis and detection Y-axis are in correspondence with the origin, X-axis and Y-axis, respectively.

Accordingly, the density measurement position adjustment method permits coordinate positions of density measurement reference points on a reference sheet to be in correspondence with coordinate positions of density measurement points on a sample sheet.

BRIEF DESCRIPTION OF THE DRAWINGS

FIG. 5(a) and 5(b) represent a view showing a movement locus of a scanning densitometer moving across the reference mark printed on the OK sheet and waveform data of density values measured by the densitometer, FIG. 7 is a cross sectional view showing the essential part of an ink supply unit in a printing machine, FIG. 11 is a view showing another example of printing arrangement state of a character "PT"

DETAILED DESCRIPTION OF THE PREFERRED EMBODIMENT

Figure 2:
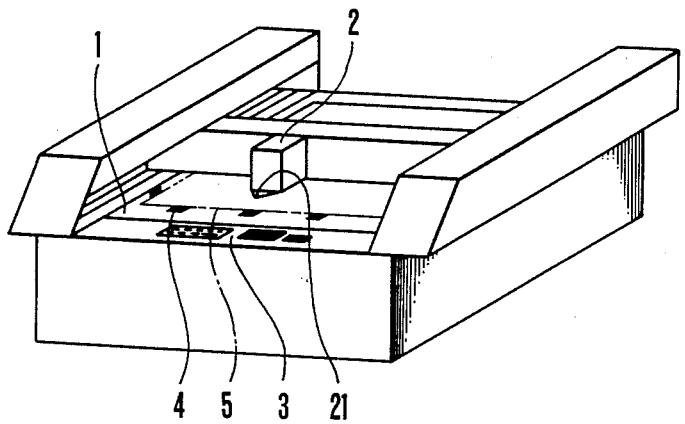
FIG. 2 is a perspective view illustrating one example of a density measurement apparatus to which the density measurement position adjustment method is applied.

A density measurement position adjustment method will be described in detail with reference to attached drawings. FIG. 2 is a perspective view illustrating an embodiment of a density measurement apparatus to which the density measurement position adjustment method is applied. This density measurement apparatus includes an X-Y coordinate table 1, a scanning densitometer 2 arranged on the X-Y coordinate table 1 so that it is movable in the X-direction of the X-Y coordinate table 1 (in the left and right directions, i.e., in a transverse direction in the figure) and in the Y-direction thereof (in the front and rear directions in the figure), and an operation unit 3 constructed as a console panel on which various switches, a display and the like are arranged. On the X-Y coordinate table 1, a paper guide 4 is provided. Thus, a paper 5 can be positioned and arranged as indicated by single dotted lines in the figure by allowing the paper end to be in contact with the paper guide 4. Further, a plurality of air holes (although not shown) are opened in one side surface of the X-Y coordinate table 1. By sucking air through these air holes, the paper 5 is held, thereby making possible to maintain flatness or evenness thereof on the X-Y coordinate table 1. The scanning densitometer 2 is constructed as a reflection type densitometer. In front of a position away from the density measurement area of its head unit, a position adjustment or registering mark 21 is provided.

Figure 3:
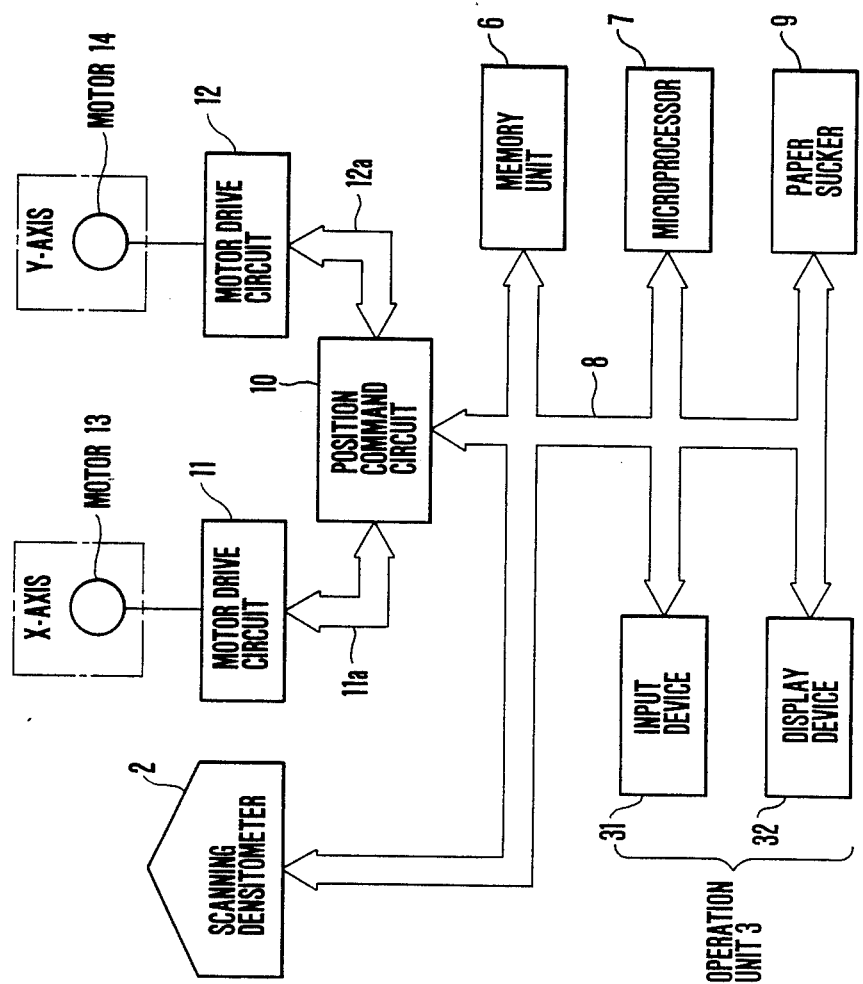
FIG. 3 is a block diagram showing the circuit arrangement of the density measurement apparatus shown in FIG. 2.

FIG. 3 is a block diagram illustrating the circuit arrangement of the above-mentioned density measurement apparatus. This density measurement apparatus includes a memory unit 6 for memorizing various data and programs, and a microprocessor 7 to execute data processing and the like in accordance with the programs constructed at the memory unit 6. The memory unit 6 and the microprocessor 7 are connected to an input device 31 and a display device 32 at the operation unit 3, a paper sucker 9, the scanning densitometer 2, and a position command circuit 10 through a data and control bus 8. Transmission and reception of various kind of information may be conducted among these components. For example, A/D conversion of a density value detected at the scanning densitometer 2 is performed in response to a command from the microprocessor 7. The density value detected which has undergone A/D conversion is memorized or stored into the memory unit 6. The position command circuit 10 conducts transmission and reception of data to and from an X-axis motor drive circuit 11 and a Y-axis motor drive circuit 12 through data and control buses 11a and 12a. The drive control of an X-axis motor 13 is performed by the X-axis motor drive circuit 11 and the drive control of a Y-axis motor 14 is performed by the Y-axis motor drive circuit 12. Namely, movements in X- and Y-directions on the X-Y coordinate table 1 of the scanning densitometer 2 are controlled by the X-axis and Y-axis motors 13 and 14, respectively. When movement quantities in X- and Y-directions and their directions are given to the position command circuit 10, rotational angles corresponding thereto are transmitted to the X-axis and Y-axis drive circuits 11 and 12. Thus, the X-axis and Y-axis motors 13 and 14 are rotationally driven by the rotational angles, respectively. It is to be noted that when the X-axis and Y-axis motors 13 and 14 are being operated, the status of completion of the operation etc. may be output to the data and control bus 8 via the position command circuit 10.

Figure 1A:
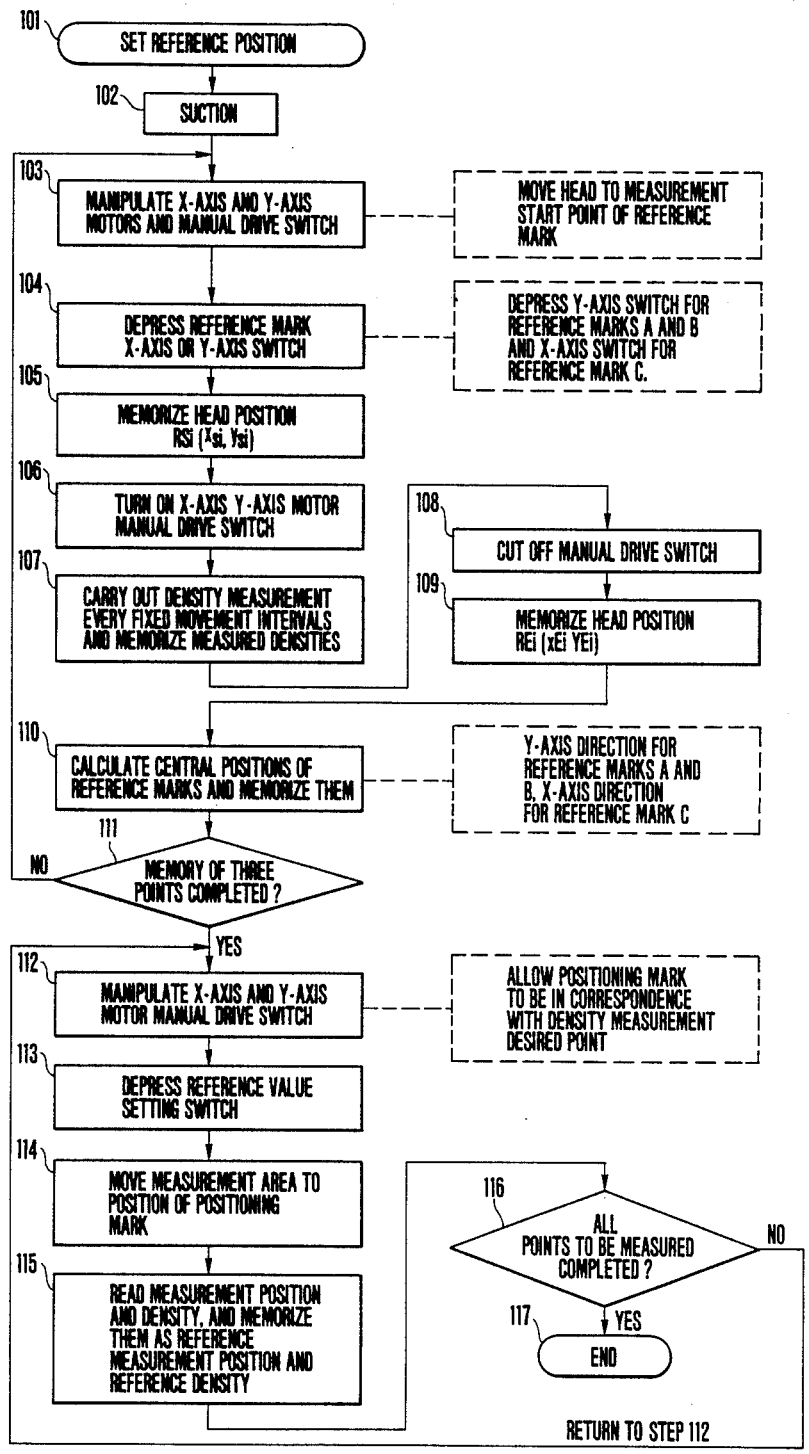
FIGS. 1(a) and 1(b) represent a flowchart showing an embodiment of a density measurement position adjustment method according to the present invention.
Figure 4:
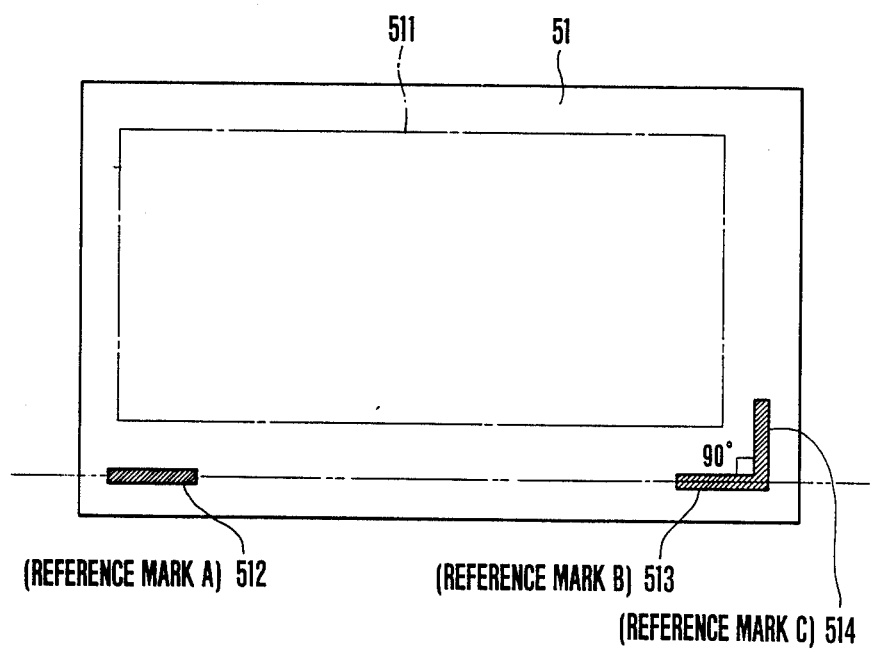
FIG. 4 is a view showing an OK sheet set on an X-Y coordinate table of the density measurement apparatus.

The density measurement position adjustment method using the density measurement apparatus thus configured will be now explained. First, an OK sheet 51 (FIG. 4) which constitutes a density specimen of a pattern (reference sheet) as the paper 5 is set on the X-Y coordinate table 1 of this density measurement apparatus. On the OK sheet 51, reference marks 512, 513 and 514 are printed as portions of the pattern depicted at the bottom of the outer peripheral portion of the pattern portion 511. These reference marks 512, 513 and 514 are painted out in the form of rectangle by predetermined widths, respectively. The reference marks 512, 513 and 514 constitute reference marks A, B and C, respectively. The reference marks A and B are such that their edges in a length direction are arranged on the same straight line and their edges in a width direction are oppositely disposed with they being spaced from each other by a predetermined distance. The reference marks B and C cross at right angles at their end portions. Namely, by adjusting the end portion of the OK sheet 51 to which such reference marks are implemented to the paper guide 4, it is positioned and arranged on the X-Y coordinate table 1. In accordance with the flowchart shown in FIG. 1(a), setting of coordinate positions on the X-Y coordinate table of density measurement desired points (density measurement reference points) and the density measurement at the coordinate points are conducted.

Namely, when the operation of the flowchart is initiated (step 101), the paper sucker 9 is activated to suck the OK sheet 51 set on the X-Y coordinate table 1 (step 102). From such a condition, X-axis and Y-axis motor manual drive switches (not shown) included in the operation unit 3 are operated to move the scanning densitometer 2, thereby allowing the position adjustment mark 21 of the scanning densitometer 2 to be in correspondence with substantially the center of the reference mark A in a width direction (step 103). Then, a Y-axis switch (not shown) is depressed (step 104). Namely, by adjusting the positioning mark 21 to the reference mark A, a density measurement area 22 of the scanning densitometer 2 is located close to the side portion of the reference mark A(512). In such a condition, the Y-axis switch is to be depressed at the step 104. A coordinate position $RSi(x_{si}, y_{si})$ of a central point P1 of the density measurement area 22 on the X-Y coordinate table 1 at this time is memorized into the memory unit 6 as a head position (step 105). Thus, by turning the Y-axis motor manual drive switch on at step 106, the point P1 of the density measurement area 22 begins moving as indicated by single dotted lines and the density measurements caused to corresponding to coordinate positions on the X-Y coordinate table every fixed movement intervals during the movement of the density measurement area 22 are conducted. Thus, density values caused to correspond to such coordinate positions are memorized into the memory unit 6 (step 107). Then, after the density measurement area 22 transverses the reference mark A, the Y-axis motor manual drive switch is cut off at step 108. A coordinate position REi($x_{Ei}$, $y_{Ei}$) of the point P1 on the X-Y coordinate table 1 at this time is memorized (step 109). FIG. 5(b) shows a density change characteristic at the time of movement of the point P1 wherein density values measured are obtained as mountain-shaped waveform data as shown in this figure. Namely, the coordinate position showing the maximum value of the mountain-shaped waveform data represents the center of the reference mark A in a width direction. The coordinates indicative of the center in the width direction are memorized at step 110. Thus, whether or not central coordinates in the width direction for three reference marks have been determined is confirmed at step 111. When they have not been determined, the program execution returns to the step 103. Namely, for the reference mark B, the positioning mark 21 of the scanning densitometer 2 is adjusted to substantially the center in the width direction of the reference mark B. Then, scanning operation is implemented in the same manner as in the case of the reference mark A. Thus, the central coordinates in the width direction thereof are determined at step 110. Further, for the reference mark C, the positioning mark 21 of the scanning densitometer 2 is adjusted to a position which is slightly shifted to the left or right at substantially the center in a length direction of the reference mark C. Then, the X-axis switch is depressed at step 104. The X-axis motor manual drive switch is turned on at step 106. Thus, the density measurement area 22 moves in the X-axis direction to scan the reference mark C. As a result, the central coordinates in the width direction are determined at step 110. Also for the reference marks B and C, density values measured are obtained as mountain-shaped data. It is to be noted that when setting is made such that the width of each reference mark is narrower than the density measurement area 22, even if the central point P1 of the density measurement area 22 does not move transversely on the reference mark in a manner rectangular thereto, the central coordinates in the width direction can be precisely detected. For color of the reference mark, any color may be used. It is preferable that the color of the reference mark is "black" or the like in view of ensurance of clear contrast with respect to the paper. For the filter of the scanning densitometer 2 at the time of detection of the reference mark, color of "visual" or any reference mark may be given by a switch to thereby automatically select a filter corresponding thereto. In addition, comparison of outputs of all filters of "visual", "Red", "Green" and "Blue" may be made to thereby employ a value which is maximum at the difference between the vertex and the bottom side of the mountain-shaped waveform.

Assuming now that the central coordinate positions in the width directions of the reference marks A, B and C are represented by A, B and C, respectively, the origin on the OK sheet 51 can be expressed as a point at which the straight line AB and a straight line drawn from C to the straight line AB intersect with each other. The coordinate transformation setting a point on the X-Y coordinate table 1 which is opposite to the origin of the OK sheet 51 as the position of origin 0 (0, 0) of the X-Y coordinate table 1 can be realized by a general numeric calculation program. In a manner similar to this, it is possible to set the straight lines AB and OC as the x-axis and y-axis, respectively. Namely, subsequently to the step 111, the microprocessor 7 determines the origin of the OK sheet 51 to consider this origin as the position of origin 0 (0, 0) on the X-Y coordinate table 1 and to consider the straight lines AB and OC as the x-axis and y-axis, respectively. At step 112, the x-axis and y-axis motor manual drive switches are operated, thereby allowing the positioning mark 21 of the scanning densitometer 2 to be in correspondence with a density measurement desired point within the pattern portion 511 on the OK sheet 51. Subsequently, when a reference value setting switch (not shown) is depressed at step 113, the density measurement area 22 moves on the basis of data indicative of quantity of positional shift between the positioning mark 21 and the density measurement area 22 to adjust the point P1 thereof to the density measurement desired point (step 114). Thus, on the basis of the movement position of the point P1 of this density measurement area 22, the coordinate position on the X-Y coordinate table 1 at the density measurement desired point is recognized and the density at this point is read, whereby they are memorized as the reference measurement coordinate position and the reference density value (step 115). By repeatedly executing such steps 112 to 115 until the result of step 116 becomes Y, it is possible to arbitrarily set a large number of density measurement reference points.

Figure 1B:
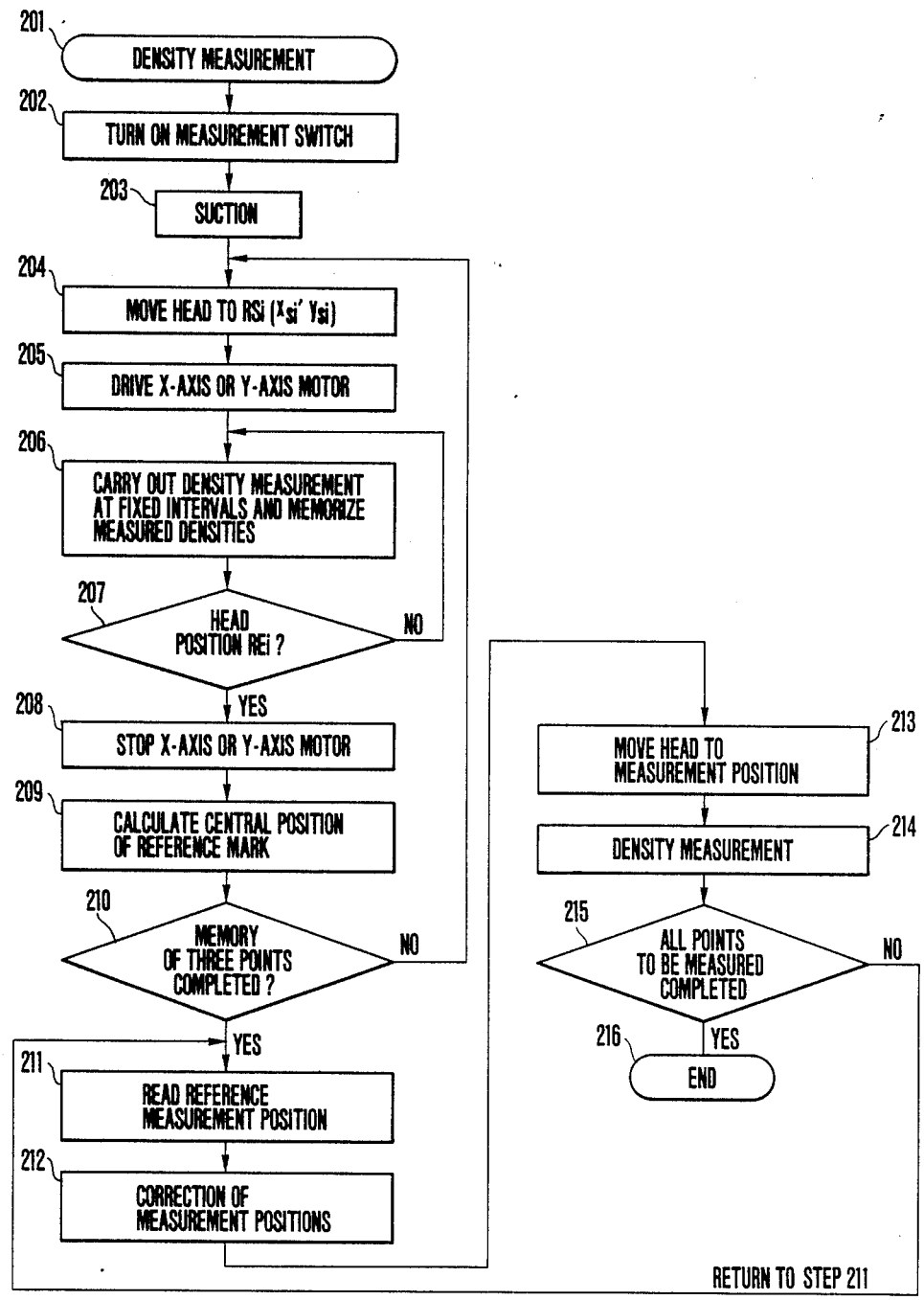

Thus, a series of works for setting density measurement reference points and reference densities using the OK sheet is completed at step 117. Then, a sample sheet (not shown) is set in place of the OK sheet 51 on the X-Y coordinate table 1 in the same manner as in the OK sheet 51. On this sample sheet, a pattern identical to that on the OK sheet is printed (reference marks A to C are also printed). At a process for printing work, it may be extracted arbitrarily for a density checking. Namely, this sample sheet is set on the X-Y coordinate table 1 to initiate the density measurements at respective points on the sample sheet which correspond to density measurement reference points on the OK sheet 51 in accordance with the flowchart shown in FIG. 1(b). First, a measurement switch (not shown) is turned on at step 202. Thus, the sample sheet is sucked and held on the X-Y coordinate table 1 (step 203) and at the same time the central point P1 of the density measurement area 22 of the scanning densitometer 2 is automatically moved to the coordinate position RSi($x_{si}$, $y_{si}$) at the step 105 which has been memorized using the OK sheet 51 (step 204). Namely, the density measurement area 22 moves to a predetermined position close to the reference mark. Then, at step 205, the X-axis motor 13 or the Y-axis motor is driven (for the reference marks A and B, the Y-axis motor 14 is driven and for the reference mark C, the X-axis motor 13 is driven), the point P1 of the density measurement area 22 begins moving and the density measurements of reference marks caused to correspond to coordinate positions on the X-Y coordinate table 1 are conducted every predetermined movement intervals. Thus, density values caused to correspond to the coordinate positions are memorized (step 206). When the point P1 of the density measurement area 22 is in correspondence with the coordinate position REi($x_{Ei}$, $y_{Ei}$) at the step 109 which has been memorized using the OK sheet 51 (step 207), the X-axis motor 13 or the Y-axis motor 14 is stopped at step 208. Thus, the central coordinate position in a width direction of the reference mark is determined on the basis of the density measurement result caused to correspond to the above-mentioned coordinate position (step 209). Namely, the steps 204 to 209 are repeatedly executed until the result of step 210 becomes Y to determine central coordinate positions A', B' and C' in respective width directions of the reference marks A, B and C. From the central coordinate positions A', B' and C' in the width directions, the origin on the sample sheet is determined. Namely, a vertical line is drawn from C' to the straight line A'B' to determine a point at which the vertical line and the straight line A'B' intersect with each other to be the origin 0' and to apply coordinate transformation to a point on the X-Y coordinate table 1 which is opposite to the origin of the sample sheet to be the position of origin 0(0, 0). In a manner similar to this, the straight lines A'B' and O'C' may be set to the x-axis and y-axis, respectively. Namely, subsequently to the step 210, the microprocessor 7 performs the above coordinate transformation to thereby consider the origin on the sample sheet as the position of origin 0(0, 0) on the X-Y coordinate table 1 and to consider the straight lines A'B' and O'C' as the x-axis and the y-axis, respectively. Namely, the coordinate position of origin and the x- and y-axis on the OK sheet 51 and the coordinate position of origin and x- and y-axis on the sample sheet are in correspondence with each other on the X-Y coordinate table 1. By reading the coordinate position (reference measurement position) of the density measurement reference point determined using the OK sheet 51 at step 211, the position of the density measurement point corresponding to the density measurement reference point is corrected (step 212). Thus, the density measurement reference point on the OK sheet 51 and the density measurement point on the sample sheet are in correspondence with each other on the coordinate of the X-Y coordinate table 1. Then, the scanning densitometer automatically moves, so that the point P1 of the density measurement area 22 is precisely located at the density measurement point on the sample sheet which is in correspondence with the coordinate position of the density measurement reference point of the OK sheet 51 (step 213). Thus, the density measurement at this point is conducted (step 214). The density measurements of density measurement points on the sample sheet corresponding to all density measurement reference points on the OK sheet are determined by repeatedly executing the steps 211 to 214 until the result of the step 215 becomes Y. The density measurement values at respective measurement points are memorized in correspondence with the reference density values at the density measurement reference points on the OK sheet 51.

Figure 6:
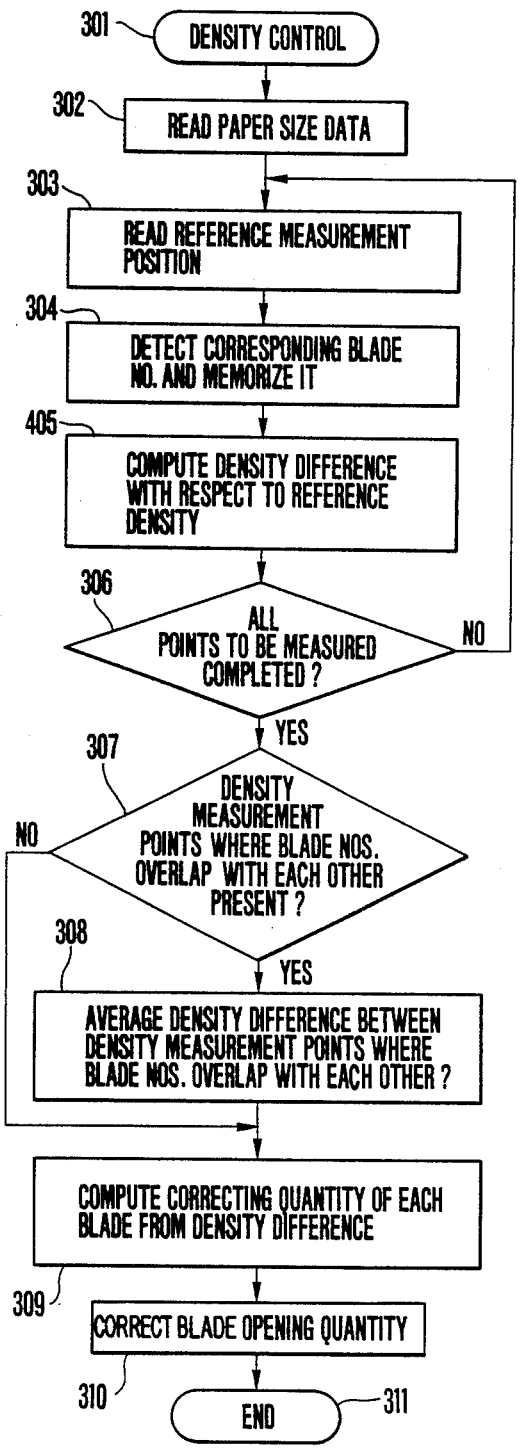
FIG. 6 is a flowchart showing a density control applied to a printing paper in a printing machine which is based on a density measurement result of a sample sheet caused to correspond to the OK sheet.
Figure 8:
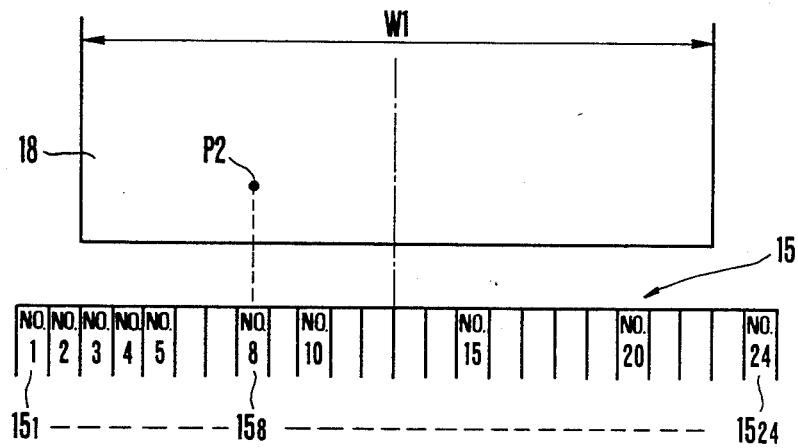
FIG. 8 is a view showing the correspondence arrangement relationship between the printing paper and the divisional blade in a printing machine.

FIG. 6 shows an example of a flowchart for conducting a pertinent control of a quantity of an ink supplied to a printing machine on the basis of the result having been explained to effect a density control of a printing picture. When the density control is initiated at step 301, data related to a paper size is read at step 302. Then, at step 303, the coordinate position on the X-Y coordinate table 1 of the density measurement reference point having been determined using the OK sheet 51 is read. A correspondence divisional blade number in the printing machine which corresponds to the coordinate position thus read is memorized (step 304). FIG. 7 is a side cross sectional view showing the essential part of the ink supply unit in the printing machine. By adjusting the opening quantity (blade opening quantity) H1 for the ink supply roller 16 of the blade 15, or by adjusting the rotational frequency of the ink supply roller 16, it is possible to adjust a supply quantity of the ink 17. The relationship in respect of the supply quantity of the ink 17, the printing density and the density difference varies in accordance with the kind of the printing machine. In this embodiment, the blade opening quantity HI is adjusted to thereby adjust an ink supply quantity, thus to perform a density control. The relationship in respect of the ink supply quantity, the printing density and the density difference is memorized in advance as data caused to correspond to a printing machine employed. As shown in FIG. 8, the blade 15 is disposed in a range broader than the width W1 of the paper 18 to be printed and is composed of a plurality of divisional blades $15_1$ to $15_{24}$ of which blade opening quantities are independently adjustable. To the divisional blades $15_1$ to $15_{24}$, predetermined blade numbers of No. 1 to No. 24 as shown are assigned, respectively. Since the paper 18 to be printed is fed to the printing machine with the paper central line indicated by single dotted lines in the figure being in correspondence with the center of the printing machine, the center in a transverse direction of the printed paper is adjusted to the center of the X-Y coordinate table by the paper guide. Accordingly, the positional relationship between the divisional blades and the density measurement points can be determined using width values of respective blades which can be known in advance. For example, where a coordinate position of a density measurement reference point corresponding to the point P2 shown in FIG. 8 is read at step 303, the divisional blade $15_8$ corresponding to the density measurement desired point thus read is selected. As a result, No. 8 which is the blade number thereof is memorized at step 304. Then, at step 305, the difference between the reference density of the density measurement reference point on the OK sheet and the density measured value of the sample sheet having been memorized in correspondence therewith is computed. By repeatedly executing the steps 303 to 305 until the result of the step 306 becomes Y, correspondence blade numbers for the all density measurement points are memorized and density differences between the all density measurement points and reference densities of the all density measurement reference points are determined. Then, at step 307, whether or not density measurement points of which blade numbers overlap with each other are present is confirmed. If density measurement points of which blade numbers overlap with each other are present, the average of the density difference between density measured values and reference densities at these density measurement points is computed at step 308. The program execution shifts to step 309. In contrast, if density measurement points of which blade numbers overlap with each other are not present, the program execution directly shifts to the step 309. At this step 309, correcting quantities of the blade opening quantities of the divisional blades corresponding to the respective density measurement points are computed on the basis of the density differences. In accordance with the correcting quantities thus computed, blade opening quantities of respective blades are corrected (step 310). By the correction of the blade opening quantities, densities at points corresponding to respective density measurement points of the printing paper 18 which is to be printed from now are precisely in correspondence with the reference densities having been determined using the OK sheet. It is to be noted that densities or density values defined in this embodiment are values obtained by implementing color separation to measure respective values of "Cyan", "Magenta", "Yellow" and "Black".

Figure 12:
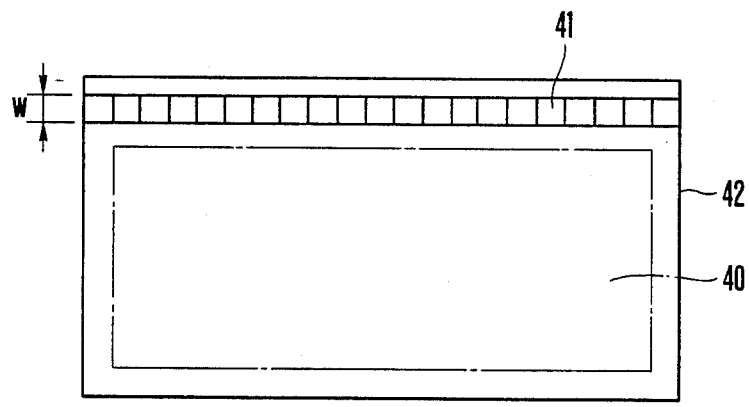
FIG. 12 is a view showing a conventional sample sheet on which a belt-shaped solid mark is printed.

As just described above, the density measurement position adjustment method according to this embodiment can conduct a density control of a pattern using narrower reference marks A to C without use of the broader solid mark 41 as shown in FIG. 12. This permits a quantity of papers to be cut after printing to be reduced to save papers accordingly. Moreover, since the density of the pattern is directly measured, the precision of the density control is extremely improved as compared to the conventional method to make a measurement using a solid mark. Further, the densities of significant portions of the pattern can be selectively supervised, resulting in high control efficiency. Furthermore, the scanning densitometer is used for detecting origins on the OK sheet and the sample sheet, resulting in simplified structure, low cost and high precision in the agreement between detection positions and measurement positions. In addition, placing a sample sheet at a predetermined position on the X-Y coordinate table 1 must be conducted with a considerable care. In accordance with this embodiment, even if a sample sheet is roughly placed, the coordinate position is corrected by making use of the software, resulting in extremely light burden on an operation.

While the reference marks A to C are printed at the bottom portion of the paper in this embodiment, it is preferable that they are printed at the central portion of the paper in an actual sense. Namely, the longitudinal length of a paper may be expanded by about 1 mm by the application of printing pressure to the paper. Where portions to which the density control is applied are not solid portions in a pattern but significant points for printing of halftone portions therein, even if there occurs positional displacement of only 0.1 mm, the measured densities greatly change at portions where tone continuously varies. For this reason, it is preferable to print reference marks at the central portion of a paper where the influence of expansion and contraction of the paper on results of computation for correction of position is small even if expansion and contraction of the paper might occur to some extent. Such an implementation permits precise density control. In addition, reference density values at density measurement reference points may be manually input. On the display device 32, coordinate positions, density measured values and the like on the X-Y coordinate table of the scanning densitometer 2 are displayed.

While the reference marks B and C are printed in a manner that they intersect with each other in this embodiment, they do not necessarily intersect with each other but may be printed with they being spaced from each other. The directions of moving the scanning densitometer after reference marks are designated are different for reference marks A and B and for reference mark A, respectively. Such directions vary depending upon how the OK sheet and the sample sheet are placed on the X-Y coordinate table. When setting is made such that the manner how the OK sheet and the sample sheet are placed is always fixed and the positional relationship of the reference marks A to C is unchanged, the sequence of scanning is determined in advance, thereby making it possible to automatically set its moving direction. In addition, when an arrangement pattern of reference marks is registered into a memory without prescribing the placement manner of the OK sheet and the sample sheet and the positional relationship with respect to respective reference marks thus to allow an operator to select the arrangement pattern, the moving direction can be automatically determined.

Figure 9:
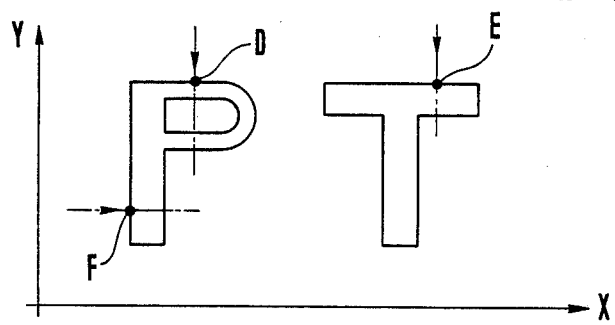
FIG. 9 is a view showing a character "PT" considered as a reference mark in the pattern.
Figure 10:
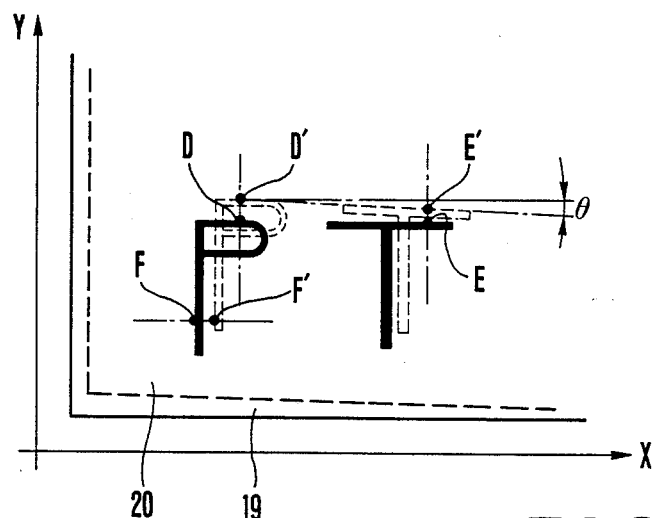
FIG. 10 is a view showing a shift of a character "PT" based on the positional shift of the OK sheet and the sample sheet set on an X-Y coordinate table.

While specified reference marks are printed at the same time when a pattern is printed in this embodiment, since crossed marks called dragon-fly marks are ordinarily printed on the printed matter, those dragon-fly marks may be utilized for the reference marks. Such reference marks are not necessarily used. Instead, any portions serving as a reference may be selected from the pattern to thereby designate lines in X- and Y-axis directions on the basis of the portions serving as the reference to consider then as reference marks. In this case, it is desirable that the center of the portion considered as the reference mark is not selected as a reference, but the position of the density gradient designated at the rising portion or at the falling portion of the boundary thereof is selected as a reference. For example, it is assumed that a character of "PT" as shown in FIG. 9 is considered as the reference mark from the pattern. In this instance, the scanning densitometer is moved in a Y-axis direction with respect to the character "PT" to thereby set a reference point D (a first reference point) at the time of rise of the density gradient. Then, by the movement of the scanning densitometer in the Y-axis direction with respect to the character "T", a reference point E (a second reference point) is set at the time of rise of the density gradient. Likewise, by the movement of the scanning densitometer in the X-axis direction with respect to the character "P", a reference point F (a third reference point) is set at the time of rise of the density gradient. Such settings are made for the OK sheet set on the X-Y coordinate table. From coordinate positions on the X-Y coordinate table of these reference points D to F, the origin, the x-axis and the y-axis are similarly determined. Thus, coordinates at density measurement desired points are memorized with them being as reference. Then, a sample sheet is set on the X-Y coordinate table. In a manner similar to the above, scans in the X-axis direction and in the Y-axis direction with respect to the character "P" and scan in the Y-axis direction with respect to the character "T" are performed using the scanning densitometer. In this instance, the set positions of the OK sheet and the sample sheet are delicately different from each other on the X-Y coordinate table. Namely, as shown in FIG. 10, a sample sheet 20 is set, e.g., at a position shifted as indicated by broken lines in this figure relative to an OK sheet 19 indicated by a solid line in this figure. Accordingly, the character "PT" of the sample sheet 20 is shifted in appearance relative to the character "PT" of the OK sheet 19 as indicated by broken lines in the figure. Thus, points corresponding to D, E and F on the OK sheet 19 obtained by the scanning operation using the scanning densitometer are obtained as D', E' and F', respectively. Namely, it is sufficient for copying with this to implement transformation of coordinate positions on the X-Y coordinate table with a view to allowing coordinate positions of reference points D', E' and F' on the sample sheet 20 to be in correspondence with coordinate positions of reference points D, E and F on the OK sheet 19. Such a coordinate transformation may be accomplished by the steps of obtaining an inclination angle θ from the coordinate positions of the reference points D' and E', correcting an aberration in a rotational direction of the character "PT" by this inclination angle θ, thereafter moving the character "PT" for the purpose of allowing the Y-coordinate of the reference point D' to be in correspondence with the Y-coordinate of the reference point D, and further moving the character "PT" for the purpose of allowing the X-coordinate of the reference point F' to be in correspondence with the X-axis of the reference point F.

It is to be noted that it is sufficient that Y-coordinates of the reference points D and E are not necessarily in correspondence with each other for the character "PT". Namely, it is enough that the upper end surface line of "P" and that of "T" are not linearly in correspondence with each other. For example, even if characters are arranged in the form of stair-steps as shown in FIG. 11, similar coordinate transformation can applied such an arrangement. In addition, while the character "PT" is considered as the reference mark in this embodiment, it is needless to say that various patterns may be similarly considered as the reference mark.

As described in detail, the density measurement position adjustment method according to the present invention comprises the step of: setting a reference sheet on which a predetermined pattern is printed on an X-Y coordinate table; designating at least three reference points referred to as first to third reference points within the pattern of the reference sheet; determining coordinate positions on the X-Y coordinate table of the three reference points; memorizing coordinate positions at density measurement reference points within the pattern of the reference sheet with a single point and two intersecting lines obtained by computation based on the coordinate positions of the reference points being as an origin, an X-axis and a Y-axis, respectively; setting a sample sheet on which the same pattern as the pattern on the reference sheet is printed on the X-Y coordinate table; detecting coordinate positions on the X-Y coordinate table of points, which correspond to the three reference points on the reference sheet, within the pattern on the sample sheet; determining a detection origin, a detection X-axis and a detection Y-axis by computation based on the coordinate positions of the points on the sample sheet; and correcting coordinate positions of density measurement points, which correspond to the density measurement points on the reference sheet, within the pattern on the sample sheet so that the detection origin, detection X-axis and detection Y-axis are in correspondence with the origin, Y-axis and Y-axis, respectively.

Accordingly, in accordance with this method, on the X-Y coordinate table, coordinate positions of density measurement reference points on the reference sheet are in correspondence with coordinate positions of density measurement points on the sample sheet. Thus, the direct supervision of the density of a pattern can be conducted extremely precisely with a lessened burden on an operator. In addition, a broader solid mark is not used as in the prior art, with the result that printing papers can be saved accordingly.

What is claimed is:

1. A method of adjusting density measurement positions including the steps of (a) setting a reference sheet on which a predetermined pattern is printed on an X-Y coordinate table, said pattern including density measurement reference points,
 (b) designating at least three reference points referred to as first to third reference points within said pattern of said reference sheet,
 (c) determining coordinate positions on said X-Y coordinate table of said at least three reference points,
 (d) computing a single point and two interacting lines based on said coordinate positions of said reference points being as an origin, an X-axis and a Y-axis, respectively,
 (e) memorizing coordinate positions at said density measurement reference points within said pattern of said reference sheet on said X-Y coordinate table, said coordinate positions being set by using said single point and two intersecting lines,
 (f) setting a sample sheet on which the same pattern as said pattern on said reference sheet, including said at least three reference points, is printed on said X-Y coordinate table,
 (g) detecting coordinate positions on said X-Y coordinate table of points, which correspond to said at least three reference points on said reference sheet, within said pattern on said sample sheet,
 (h) determining a detection origin, a detection X-axis and a detection Y-axis by computation based on said coordinate positions of said at least three reference points on said sample sheet, and
 (i) correcting coordinate positions of density measurement points, which correspond to said density measurement points on said reference sheet, within said pattern on said sample sheet so that said detection origin, detection X-axis and detection Y-axis are in correspondence with said origin, X-axis and Y-axis, respectively.

2. A density measurement position adjustment method as set forth in claim 1, wherein said first reference point is present on a first axis set on said reference sheet, said second reference point is present on said first axis or an axis parallel thereto in a manner that said second reference point is spaced apart from said first reference point, and said third reference point is present on a second axis vertical to said first axis.

3. A density measurement position adjustment method as set forth in claim 2, wherein said reference points are in the form of reference marks having a predetermined area printed in advance on said reference sheet as portions of said pattern thereon, respectively.

4. A density measurement position adjustment method as set forth in claim 3, wherein coordinate positions of said reference points are determined on the basis of changes in densities measured by scanning said respective reference marks using a scanning densitometer.

5. A density measurement position adjustment method as set forth in claim 4, wherein coordinate positions of said reference points are determined as coordinate positions detected when the central point of a density measurement area of said scanning densitometer is positioned at each central portion of said reference marks.

6. A density measurement position adjustment method as set forth in claim 5, wherein said reference marks have a width narrower than said density measurement area of said scanning densitometer.

7. A density measurement position adjustment method as set forth in claim 5, wherein when the central coordinate positions in the width directions of said first to third reference marks are denoted by A, B and C, respectively, an origin on said reference sheet is expressed as point 0 at which the straight line AB and a straight line perpendicularly drawn from C intersect with each other.

8. A density measurement position adjustment method as set forth in claim 7, wherein said origin on said reference sheet is transformed to the origin on said X-Y coordinate table by performing a predetermined coordinate transformation.

9. A density measurement position adjustment method as set forth in claim 5, wherein straight lines AB and OC on said reference sheet are transformed to the X-axis and the Y-axis on said X-Y coordinate table by performing a predetermined coordinate transformation, respectively.

10. A density measurement position adjustment method as set forth in claim 5, wherein the central coordinate positions in the width directions of points, which correspond to said reference points on said reference sheets, on said sample sheet are denoted by A', B' and C', respectively, an origin on said sample sheet is expressed as a point 0' at which the straight line A'B' and a straight line perpendicularly drawn from C' intersect with each other.

11. A density measurement position adjustment method as set forth in claim 10, wherein said origin on said sample sheet is transformed to the origin on said X-Y coordinate table by performing a predetermined coordinate transformation.

12. A density measurement position adjustment method as set forth in claim 10, wherein said straight lines A'B' and O'C' on said reference sheet are transformed to the X-axis and the Y-axis on said X-Y coordinate table by performing a predetermined coordinate transformation, respectively.

13. A density measurement position adjustment method as set forth in claim 3, wherein the densities measured by a scanning densitometer are obtained as mountain-shaped data, respectively.

14. A density measurement position adjustment method as set forth in claim 3, wherein said first and second reference mark are provided in a manner that their edges in a length direction are disposed on the same straight line and their edges in a width direction are oppositely disposed with they being spaced from each other by a predetermined distance, and said second and third reference marks perpendicularly intersect with each other at their end portions.

15. A density measurement position adjustment method as set forth in claim 3, wherein said reference marks have a rectangular area painted out.

16. A density measurement position adjustment method as set forth in claim 15, wherein said reference marks are colored black.

17. A density measurement position adjustment method as set forth in claim 1, wherein said reference points are obtained by utilizing, as reference marks, predetermined portions of said pattern itself on said reference sheet respectively.

18. A density measurement position adjustment method as set forth in claim 17, wherein coordinate positions of said reference points are determined on the basis of changes in densities measured by scanning said respective reference marks using a scanning densitometer.

19. A density measurement position adjustment method as set forth in claim 18, wherein coordinate positions of said reference points are determined as coordinate positions detected when the central point of density measurement area of said scanning densitometer transverse over each boundary portion of said predetermined portions of said reference marks.

20. A density measurement position adjustment method as set forth in claim 1, wherein when there is a difference between set positions on said X-Y coordinate table of said reference sheet and said sample sheet, said step for correction includes a step for performing a coordinate transformation in order to adjust the coordinate positions of said points, which correspond to said reference points, on said sample sheet to the coordinate positions of said reference points on said reference sheet.

21. A density measurement position adjustment method as set forth in claim 20, wherein said coordinate transformation is performed by determining an inclination angle defined by said points, which correspond to said reference points, on said sample sheet based on computation using said coordinate position thereof to correct an aberration in a rotational direction using said inclination angle, thereafter to shift corresponding points on said sample sheet so that said coordinate positions of said points on said sample sheet are in correspondence with those of said reference points on said reference sheet.

22. A density measurement position adjustment method as set forth in claim 21, wherein any one of said second and third reference points is not present on an axis on which said first reference point is present.

23. A density measurement position adjustment method as set forth in claim 22, wherein said correction of said coordinate positions of density measurement positions within said pattern on said sample sheet can be made by making use of substantially the same coordinate transformation as said coordinate transformation.

24. A density measurement position adjustment method as set forth in claim 2, wherein said reference marks are printed approximately at the central portion of said reference sheet.

25. A density measurement position adjustment method as set forth in claim 1, wherein the operation for adjusting density measurement positions is made on the basis of changes in densities measured by scanning respective reference marks using a scanning densitometer.

26. A density measurement position adjustment method as set forth in claim 25, wherein a circuit for performing said operation using said scanning densitometer includes a computer-controlled circuit, a position command circuit including motor drive circuits for driving X- and Y-axis motors, and a paper sucker for sucking said reference and sample sheets onto said X-Y coordinate table.

27. A density measurement position adjustment method as set forth in claim 26, wherein said computer-controlled circuit comprises a memory unit for memorizing various data and programs, a microprocessor for performing data processings in accordance with a program constructed in said memory unit, and an operation unit including an input device for setting necessary input data such as reference density values at said reference measurement reference points and a display device on which coordinate positions, density measured values are displayed.

* * * * *